(12) United States Patent
Stevenson et al.

(10) Patent No.: US 6,275,369 B1
(45) Date of Patent: Aug. 14, 2001

(54) EMI FILTER FEEDTHOUGH TERMINAL ASSEMBLY HAVING A CAPTURE FLANGE TO FACILITATE AUTOMATED ASSEMBLY

(76) Inventors: Robert A. Stevenson, 15349 Iron Canyon Rd., Canyon Country, CA (US) 91351; Donald K. Haskell, 880 Mahogany Dr., Minden, NV (US) 89423; Richard L. Brendel, 1551 Jefferson Dr., Carson City, NV (US) 89706

( * ) Notice: Subject to any disclaimer, the term of this patent is extended or adjusted under 35 U.S.C. 154(b) by 0 days.

(21) Appl. No.: 09/460,879

(22) Filed: Dec. 14, 1999

Related U.S. Application Data

(63) Continuation-in-part of application No. 08/969,480, filed on Nov. 13, 1997, now Pat. No. 6,008,980.

(51) Int. Cl.$^7$ ..................................... H01G 4/35
(52) U.S. Cl. ................ 361/302; 361/303; 361/306.1; 361/309
(58) Field of Search ................ 361/302, 306.1, 361/309, 306.2, 303, 307, 320, 321.6, 321.5; 607/2, 5

(56) References Cited

U.S. PATENT DOCUMENTS

| | | |
|---|---|---|
| 2,756,375 | 7/1956 | Peck . |
| 3,235,939 | 2/1966 | Rodriguez et al. . |
| 3,920,888 | 11/1975 | Barr . |
| 4,083,022 | 4/1978 | Nijman . |
| 4,144,509 * | 3/1979 | Boutros ............... 333/181 |
| 4,148,003 | 4/1979 | Colburn et al. . |
| 4,152,540 | 5/1979 | Duncan et al. . |
| 4,220,813 | 9/1980 | Kyle . |
| 4,247,881 | 1/1981 | Coleman . |
| 4,314,213 | 2/1982 | Wakino . |
| 4,352,951 | 10/1982 | Kyle . |
| 4,362,792 | 12/1982 | Bowsky et al. . |
| 4,421,947 | 12/1983 | Kyle . |
| 4,424,551 | 1/1984 | Stevenson . |
| 4,456,786 | 6/1984 | Kyle . |
| 4,737,601 | 4/1988 | Gartzke . |
| 4,741,710 | 5/1988 | Hogan et al. . |
| 5,032,692 | 7/1991 | DeVolder . |
| 5,070,605 | 12/1991 | Daglow et al. . |
| 5,333,095 | 7/1994 | Stevenson et al. . |
| 5,825,608 * | 10/1998 | Duva et al. ............... 361/302 |
| 5,905,627 * | 5/1999 | Brendel et al. ............... 361/302 |

* cited by examiner

Primary Examiner—Anthony Dinkins
(74) Attorney, Agent, or Firm—Kelly Bauersfeld Lowry & Kelley, LLP

(57) ABSTRACT

An EMI filter feedthrough terminal assembly includes at least one conductive terminal pin, a feedthrough filter capacitor which has a passageway through which the terminal pin extends, and a conductive substrate through which the terminal pin passes in non-conductive relation. The conductive substrate includes a capture flange having a height that is less than an axial thickness of the capacitor and which is configured to at least partially surround an outer periphery of the capacitor. The height of the capture flange is preferably one-quarter to three-quarters of the axial thickness of the capacitor. A first set of capacitor electrodeplates is conductively coupled to the terminal pin, and a second set of electrode plates is conductively coupled to the capture flange by means of a thermal-setting conductive material disposed between the outer periphery of the capacitor and the capture flange. A related process is provided for manufacturing an EMI filter feedthrough terminal assembly that advantageously utilizes the capture flange.

19 Claims, 5 Drawing Sheets

EMI FILTER FEEDTHOUGH TERMINAL ASSEMBLY HAVING A CAPTURE FLANGE TO FACILITATE AUTOMATED ASSEMBLY

RELATED APPLICATION

This is a continuation-in-part of U.S. patent application Ser. No. 08/969,480, filed Nov. 13, 1997, now U.S. Pat. No. 6,008,980 and entitled HERMETICALLY SEALED EMI FEEDTHROUGH FILTER CAPACITOR FOR HUMAN IMPLANT AND OTHER APPLICATIONS.

BACKGROUND OF THE INVENTION

This invention relates generally to feedthrough capacitor terminal pin subassemblies and related methods of construction, particularly of the type used in implantable medical devices such as cardiac pacemakers and the like, to decouple and shield undesirable electromagnetic interference (EMI) signals from the device. More specifically, this invention relates to a simplified feedthrough terminal pin sub-assembly which incorporates a capture flange to facilitate assembly by automation.

Feedthrough terminal assemblies are generally well known for connecting electrical signals through the housing or case of an electronic instrument. For example, in implantable medical devices such as cardiac pacemakers, defibrillators, or the like, the terminal pin assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. However, the feedthrough terminal pins are typically connected to one or more lead wires which effectively act as an antenna and thus tend to collect stray electromagnetic interference (EMI) signals for transmission into the interior of the medical device. In prior devices, such as those shown in U.S. Pat. Nos. 5,333,095 and 4,424,551 (the contents of which are incorporated herein), the hermetic terminal pin sub-assembly has been combined in various ways with a ceramic feedthrough capacitor filter to decouple electromagnetic interference (EMI) signals into the housing of the medical device.

With reference to FIG. 1, in a typical prior art unipolar feedthrough filter assembly 20 (as described in U.S. Pat. No. 5,333,095), a round/discoidal (or rectangular) ceramic feedthrough filter capacitor 22 is combined with a hermetic terminal pin assembly 24 to suppress and decouple the undesired interference or noise transmission along a terminal pin 26. The feedthrough capacitor is coaxial, having two sets of electrode plates 28, 30 embedded in spaced relation within an insulative dielectric substrate or base 32, formed typically as a ceramic monolithic structure. One set of the electrode plates 28 is electrically connected at an inner diameter cylindrical surface of the coaxial capacitor structure to a conductive terminal pin 26 utilized to pass the desired electrical signal or signals. A second set of electrode plates 30 is coupled at an outer diameter surface of the discoidal capacitor 22 to a cylindrical ferrule 34 of conductive material, which is electrically connected in turn to the conductive housing of the electronic device. The number and dielectric thickness spacing of the electrode plate sets 28, 30 varies in accordance with the capacitor value and the voltage rating of the coaxial capacitor 22. The second set of electrode plates 30 (or "ground" plates) are coupled in parallel together by a metallized layer 36 which is either fired, sputtered or plated onto the ceramic capacitor. The metallized band 36, in turn, is coupled to the ferrule by conductive adhesive, soldering, brazing, welding, or the like. The first set of electrode plates 28 (or "active" plates) are coupled in parallel together by a metallized layer 38 which is either glass frit fired or plated onto the ceramic capacitor. This metallized band 38, in turn, is mechanically and electrically coupled to the leads wire(s) 26 by conductive adhesive, soldering or the like.

In operation, the coaxial capacitor 22 permits passage of relatively low frequency electrical signals along the terminal pin 26, while shielding and decoupling/attenuating undesired interference signals of typically high frequency (such as EMI from cellular telephones or microwave ovens) to the conductive housing. Feedthrough capacitors of this general type are available in unipolar (one), bipolar (two), tripolar (three), quadpolar (four), pentapolar (five), hexpolar (six), and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy which is electrically and mechanically coupled to the hermetic terminal pin assembly 24, which is in turn electrically coupled to the coaxial feedthrough filter capacitor 22. As a result, the filter capacitor and terminal pin assembly prevents entrance of interference signals to the interior of the pacemaker housing, wherein such interference signals could otherwise adversely affect the desired cardiac pacing or defibrillation function.

One drawback of the feedthrough filter assembly 20 described above is that it does not lend itself well to automated assembly using robots. More specifically, U.S. Pat. No. 5,333,095 (FIG. 1) discloses an EMI filter capacitor 22 which is essentially surface mounted onto the hermetic seal or titanium casing 40 of an implantable medical device. In U.S. Pat. No. 5,333,095, connections from the perimeter or outside diameter of the capacitor 22 are generally made by hand dispensing a conductive thermal-setting material 42 such as a conductive polyimide around the circumference of said capacitor. In a similar manner, electrical contact is made between the lead wires 26 and the inside diameter of the feedthrough capacitor 22. This construction technique results in a highly reliable and high performance EMI feedthrough capacitor; however, the handwork is very time consuming and is therefore costly. The design of the feedthrough terminal assembly 20 of U.S. Pat. No. 5,333,095 does not lend itself to automation. That is because there is no reservoir to contain the conductive thermal-setting material 42 such that it could be easily dispensed using an automated epoxy dispenser or robot. In addition, the lack of a capacitor guide combined with the necessity to hand dispense the conductive thermosetting material 42 around the capacitor outside diameter results in a substantial number of visual rejects. These visual rejects are typically noted by the customer at receiving inspection and are related in variations in the amount and location of the hand dispensed connection material.

Referring to FIG. 2, U.S. Pat. No. 4,424,551 teaches the installation of a circular or discoidal feedthrough capacitor 22 completely inside of a cylindrical cavity. As taught in the '551 patent, it is possible to automate this assembly by flooding the entire top surface of the ceramic capacitor 22 with a conductive thermal-setting material 42 and then centrifuging this assembly such that the conductive thermal-setting material (through centrifugal acceleration forces) is moved into the inner and outer cavities between the capacitor outer diameter and ferrule 34, and between capacitor inner diameter and lead(s) 26. The outer cavities as defined in the U.S. Pat. No. 4,424,551 specifically mean the space between the capacitor 22 outside diameter and the inside of the cylindrical ferrule 34, and the inner cavity is the space between the lead wire 26 and the inside diameter of the feedthrough capacitor. There are a number of significant problems associated with the approach of U.S. Pat. No. 4,424,551 including the fact that the package is not particularly volumetrically efficient. That is, the cylindrical ferrule 34 extends well above the ceramic capacitor 22 and a nonconductive epoxy coating (cap) 44 is placed over the top of the capacitor. Not only is this top covering volumetrically inefficient, it also does not match the thermal coefficient of expansion of the relatively brittle ceramic capacitor. This can lead to both moisture and micro-cracking problems within the ceramic capacitor 22 structure itself. Another problem is that the epoxy cap 44 material tends to act as an adjunct hermetic seal which can mask a leaking gold braze or glass hermetic seal underneath. That is, the hermetic seal test is typically done with helium where such test is done in a few seconds. The bulk permeability of such epoxy coverings/caps 44 is such that it might take several minutes for the helium to penetrate through such a covering.

Accordingly, there is a need for a novel feedthrough filter terminal assembly that addresses the drawbacks noted above in connection with the prior art. In particular, a novel terminal assembly is needed which accommodates automated dispensing or robotic installation of assembly components. Additionally, the improved feedthrough filter terminal assembly should lend itself to standard manufacturing processes such that cost reductions can be realized immediately. Of course, the new design must be capable of effectively filtering out undesirable electromagnetic interference (EMI) signals from the target device. The present invention fulfills these needs and provides other related advantages.

SUMMARY OF THE INVENTION

The EMI filter feedthrough terminal assembly comprises, generally, at least one conductive terminal pin, a feedthrough filter capacitor which has a passageway through which the terminal pin extends, and a conductive substrate which includes a capture flange that has a height which is less than an axial thickness of the capacitor and which is configured to at least partially surround an outer periphery of the capacitor. The feedthrough filter capacitor has first and second sets of electrode plates. The terminal pin extends through the passageway of the capacitor in conductive relation with the first set of electrode plates. In a preferred form, the height of the capture flange is one quarter to three-quarters of the axial thickness of the capacitor. The second set of electrode plates is conductively coupled to the capture flange.

A thermal-setting conductive material, solder preform, braze ring or solder paste is disposed between the outer periphery of the capacitor and the capture flange, to conductively couple the second set of electrode plates to the conductive substrate. The thermal-setting conductive material is taken from the group of conductive epoxy, conductive polyimide, or solder paste.

An insulator is supported by the conductive substrate through which the terminal pin passes. The insulator may be spaced from a face of the capacitor to form an air gap therebetween. In this configuration, the capture flange entirely surrounds the outer periphery of the capacitor, and the conductive material is disposed between discrete segments of the outer periphery of the capacitor and the capture flange.

The capture flange may further include a countersink to facilitate robotic dispensing of a conductive thermal-setting material or solder ring or solder paste between the outer periphery of the capacitor and the capture flange. The peripheral edges of the capacitor may also be axially rounded to facilitate automated manufacture of the feedthrough terminal assembly.

Noble metal hermetic terminal seal joints may be provided between the terminal pin and the feedthrough filter capacitor, the feedthrough filter capacitor and the conductive substrate and/or the insulator.

The invention also resides in a process for manufacturing an EMI filter feedthrough terminal assembly. The process comprises the steps of placing a conductive ferrule having a capture flange into a holding fixture, and forming a partial seat or full O-ring of non-conductive thermal-setting material onto the ferrule within the capture flange. The seat or O-ring material is then pre or fully cured. A feedthrough filter capacitor is loaded into the capture flange on top of the seat or O-ring, and a conductive thermal-setting material is dispensed between outer diameter of the feedthrough filter capacitor and the capture flange. The conductive thermal-setting material between the outer diameter of the feedthrough filter capacitor and the capture flange is cured to complete the basic assembly. Alternatively, the seat/O-ring non conductive material and the conductive material may be cured at one time (co-curing).

The process includes the steps of curing the O-ring subsequent to the loading step and prior to the dispensing step, and centrifuging the assembly subsequent to the dispensing step and prior to the curing step. This packs the conductive thermal-setting material to make sure it is free of air voids. The process further includes the step of conductively coupling the feedthrough filter capacitor to one or more feedthrough lead wires Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 10 is an enlarged fragmented sectional view taken of the area indicated by the line 10 of FIG. 9, illustrating a countersink in the capture flange to facilitate the automated dispensing of a conductive thermal-setting material, solder preform, solder paste, braze material or the like.

DETAILED DESCRIPTION OF THE PREFERRED EMBODIMENTS

Figure 7:
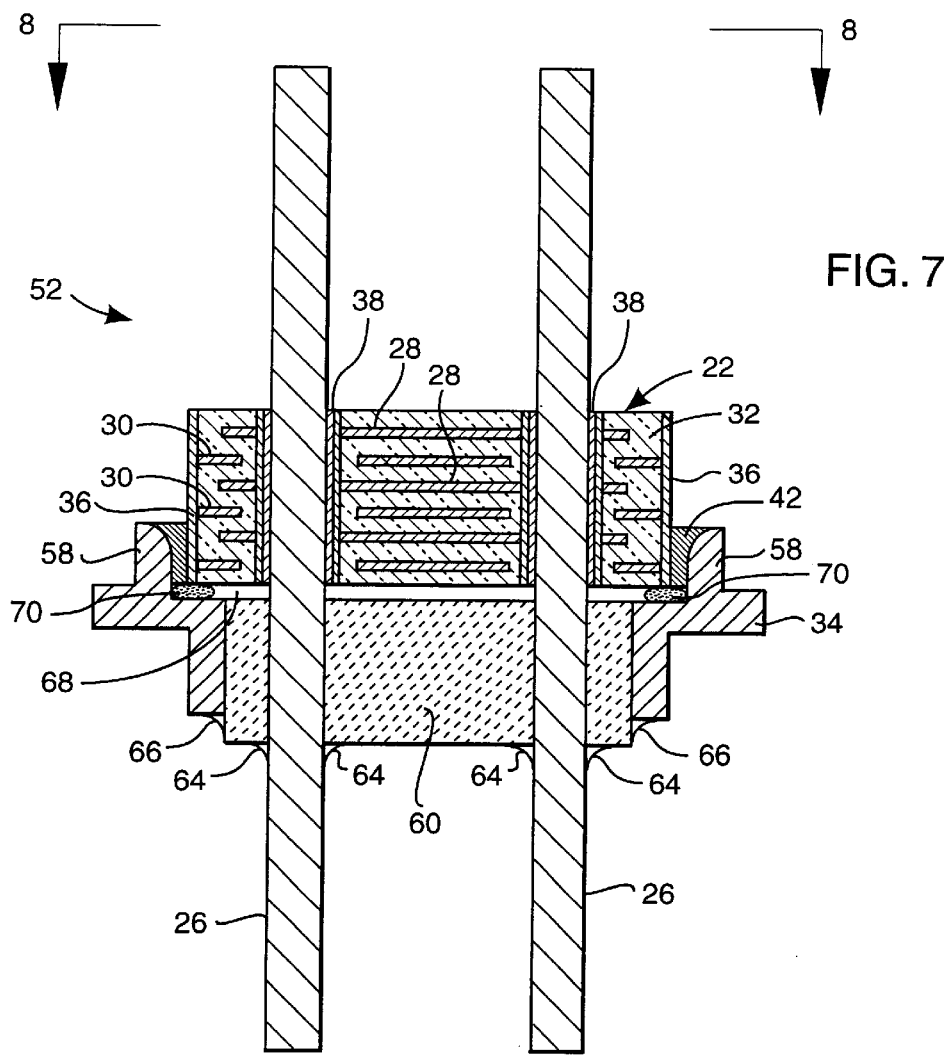
FIG. 7 is a sectional view similar to that shown in FIG. 4, illustrating an alternate configuration of components for an EMI filter feedthrough terminal assembly having a capture flange to facilitate automated assembly in accordance with the present invention.
Figure 8:
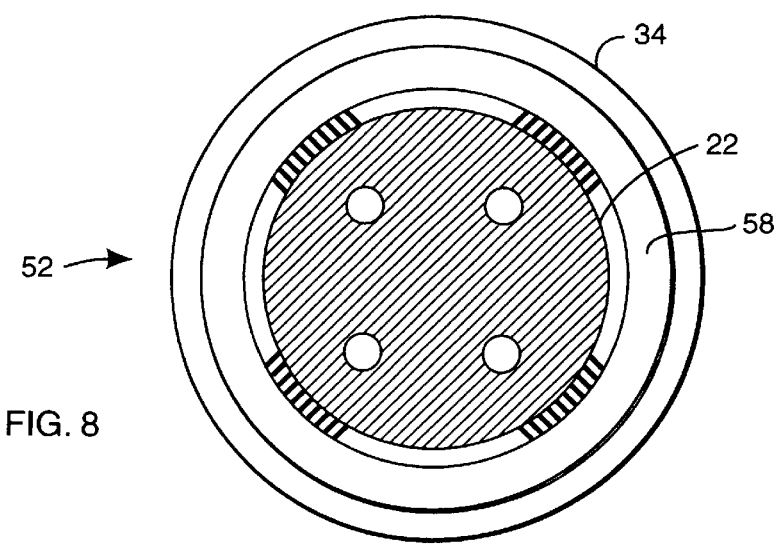
FIG. 8 is a top plan view taken generally along the line 8—8 of FIG. 7.
Figure 9:
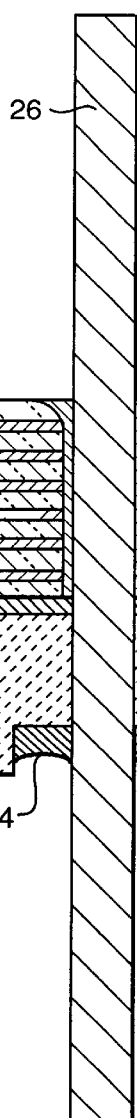
FIG. 9 is a sectional view similar to FIGS. 4 and 7, illustrating yet another configuration of components for an EMI filter feedthrough terminal assembly having a capture flange to facilitate automated assembly in accordance with the present invention.
Figure 9:
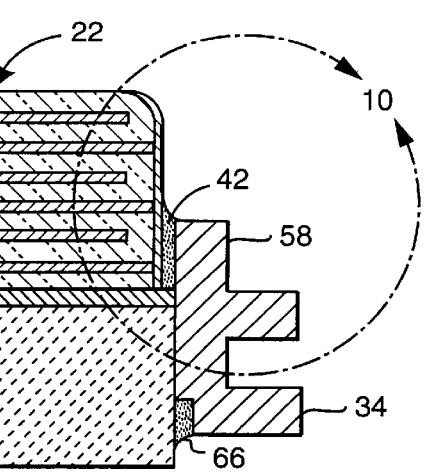
Figure 10:
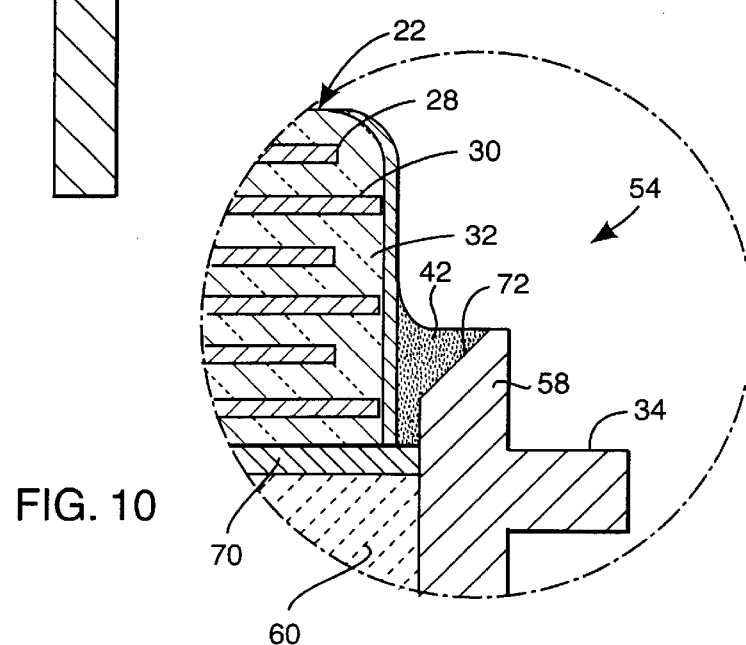

As shown in the drawings for purposes of illustration, the present invention is concerned with a novel EMI filter feedthrough terminal assembly generally designated in FIGS. 3–6 by the reference number 50, in FIGS. 7–8 by the reference number 52, and in FIGS. 9–10 by the reference number 54. In this description, functionally equivalent elements of the various embodiments (including the prior art assemblies 20 and 21 of FIGS. 1 and 2) share the same reference number. The improved feedthrough filter capacitor assemblies 50–54 comprise, generally, at least one conductive terminal pin 26, a conductive substrate or ferrule 34 through which the terminal pin passes in non-conductive relation, and a ceramic feedthrough filter capacitor 22. The capacitor 22 comprises a ceramic housing 32 that supports in spaced relation first and second sets of electrode plates 28 and 30. A passageway 56 is provided through the feedthrough filter capacitor 22 through which the terminal pin 26 extends in conductive relation with the first set of electrode plates 28. The second set of electrode plates 30 is, in turn, conductively coupled to the conductive substrate 34.

The present invention relates to a simplified and reduced cost ceramic feedthrough capacitor assembly and related installation method including one or more EMI filter capacitors 22, which are mounted in such a way such that they become a continuous part of the overall electromagnetic shield and the hermetic seal. This invention is particularly designed for use in cardiac pacemakers (bradycardia devices), cardioverter defibrillators (tachycardia), congestive heart failure stimulators, neuro-stimulators, internal drug pumps, cochlear implants, and other medical implant applications. This invention is also applicable to a wide range of other EMI filter applications, such as military or space electronic modules where it is desirable to preclude the entry of EMI into a hermetically sealed housing or shielded enclosure containing sensitive electronic circuitry. In accordance with the present invention, a capture flange 58 is included as part of the ferrule 34 to provide a convenient space for automated dispensing or robotic installation of the components while solving the problems noted above regarding the prior art FIGS. 3, 4, 7, 9 and 10 illustrate ceramic feedthrough assemblies 50–54 with a capture flange-type ferrule coming part way up the outside diameter of said capacitor structure 22. This capture flange 58 provides a convenient space around the outside perimeter or circumference of said capacitor whereby a robot or automatic dispensing system can dispense a thermal-setting conductive material 42 such as a conductive polyimide, solder paste, solder preform or braze preform. By not having the capture flange 58 extend all the way above the top of the capacitor 22, as is shown and described in U.S. Pat. No. 4,424,551 (FIG. 2), this then greatly reduces the amount of heat that is conducted to the ceramic capacitor 22 during laser welding of the terminal assembly 50–54 into the titanium housing of an implantable medical device. Because the heat is limited, it is now possible to use solder to make the connection between the lead wire 26 and the inside diameter of the feedthrough capacitor(s) 22 (solder reflow temperature is 200° C. to 300° C. whereas conductive polyimide cures at 500° C. or more). This then leads to the ability to completely automate the device in such a way that the capacitor 22 is contained partially with a capture flange 58, and the outside connection is made with an conductive thermal-setting material 42, and the lead wire connections are made with solder.

Figure 1:
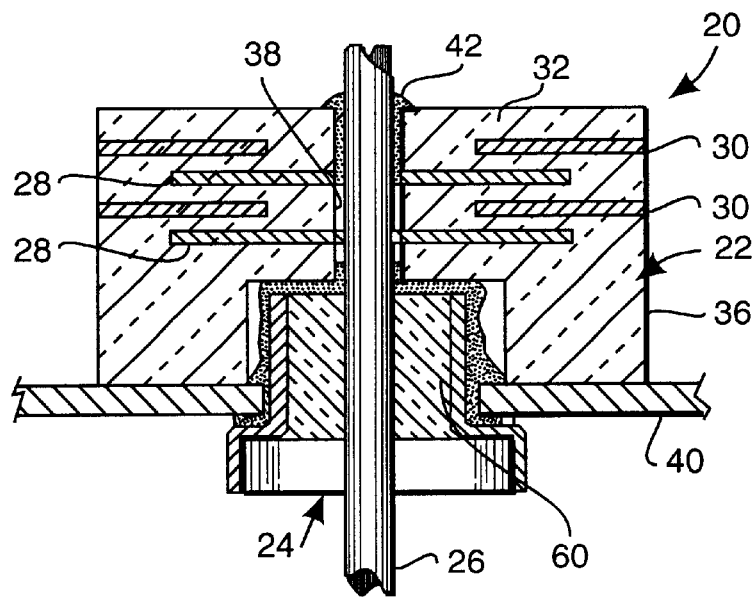
FIG. 1 is a fragmented sectional view of a prior art EMI filter feedthrough terminal assembly shown in U.S. Pat. No. 5,333,095.
Figure 2:
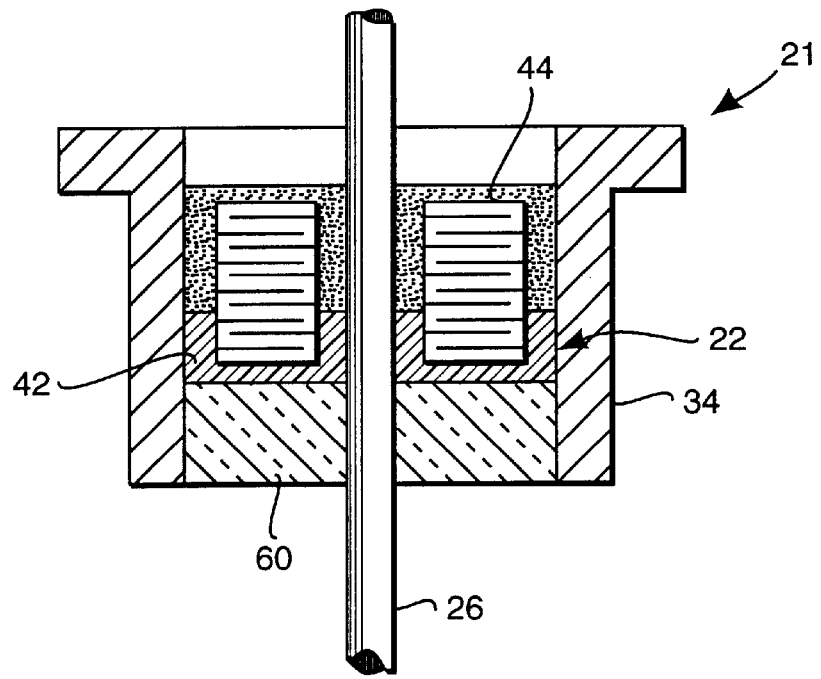
FIG. 2 is a fragmented sectional view of another prior art EMI filter feedthrough terminal assembly shown in U.S. Pat. No. 4,424,551.

With reference to FIGS. 3–6, there is shown a quadpolar feedthrough filter terminal assembly 50 constructed in accordance with the principles of the present invention, wherein multiple feedthrough capacitors 22 are provided in a substantially coplanar array within a common base structure, with each capacitor 22 being placed in association with a respective terminal pin 26. This feedthrough terminal is essentially the same as shown in FIG. 1 of U.S. patent application Ser. No. 08/969,480 now U.S. Pat. No. 6,008,980. The feedthrough filter terminal assembly 50 of FIGS. 3–6 illustrates the use of a glass or alumina insulator 60 to provide a buffer between a fluid environment that could be harmful to the internal components of the feedthrough filter capacitor 22. In particular, it is sometimes desirable, especially in medical implant applications, to provide a fluid impervious insulator 60 to protect the sets of electrode plates 28 and 30. Both the insulator 60 and the ceramic feedthrough filter capacitor 22 are bonded to the ferrule 34, which, as shown, includes a standard H-flange 62. The H-flange 62 would, in turn, be connected to another portion of the conductive substrate, such as the pacemaker housing. The connection between the insulator 60 and the ferrule 34, as well as between the pins 26 and the insulator 60, is effected by means of hermetic seal joints 64 and 66.

The first hermetic seal joint 64 between the terminal pin 26 and the insulator 60 is created by applying a metallization layer to the ceramic housing 32 adjacent to an end of the extended passageway 56 through the insulator 60. A metal braze is then applied over the metallization layer to mechanically attach the terminal pin 26 to the metallization layer. More particularly, the metallization layer is created by first sputtering down an adhesion layer such as titanium. Next nickel is sputtered or electroplated over the adhesion layer. Finally, and especially in the case of a medical implant application, gold is sputtered or electroplated over the nickel. Alternatively, the metallization layer may be deposited by plasma/electric arc discharge or electro-plating techniques. The same technique may also be utilized to create the second hermetic seal joint 66 between the outer periphery of the insulator 60 and the ferrule 34.

Figures 3, 4:
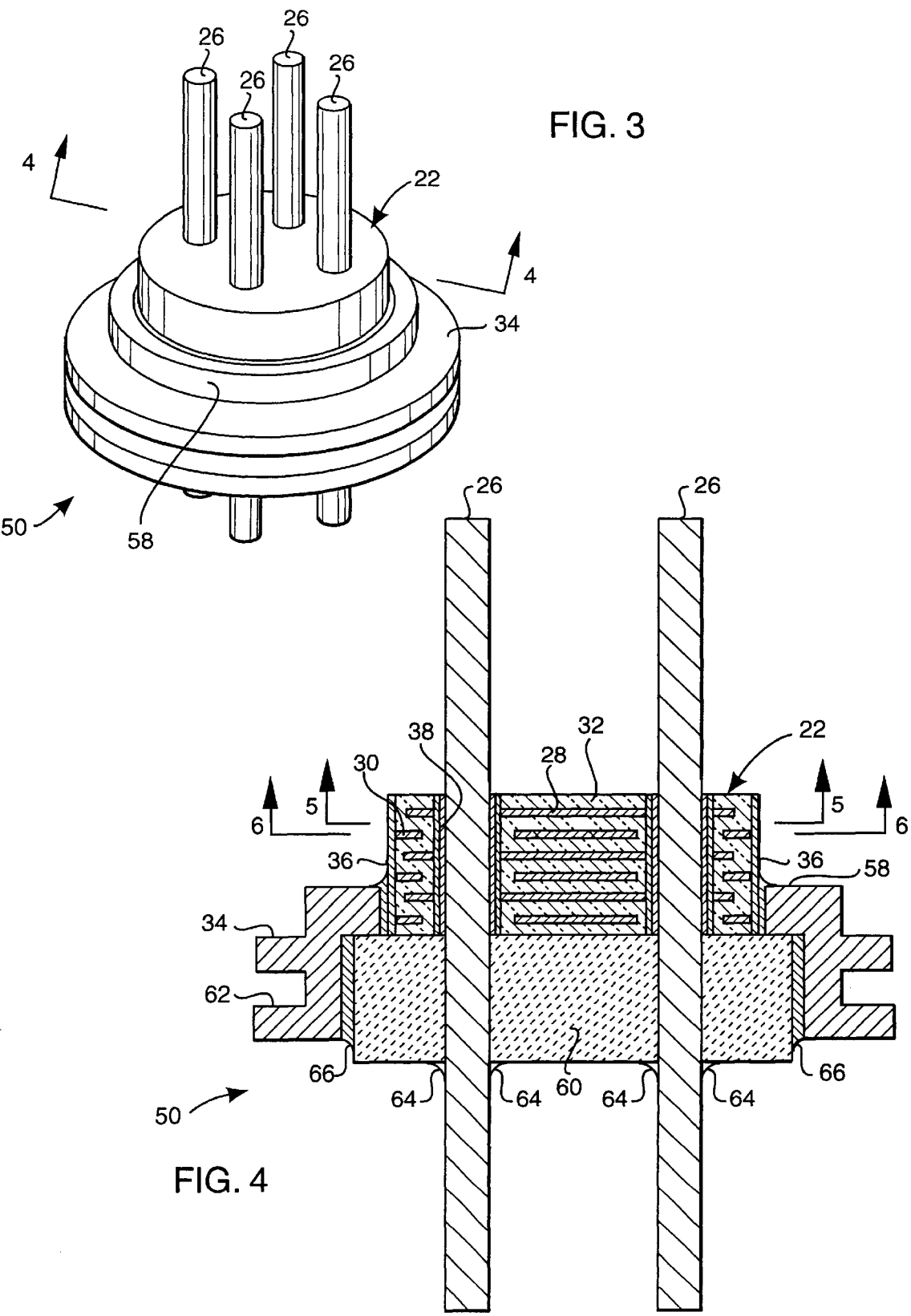
FIG. 3 is a perspective view of an EMI filter feedthrough terminal assembly having a capture flange to facilitate automated assembly, embodying aspects of the present invention.
FIG. 4 is an enlarged sectional view taken generally along the line 4—4 of FIG.3.
Figure 5:
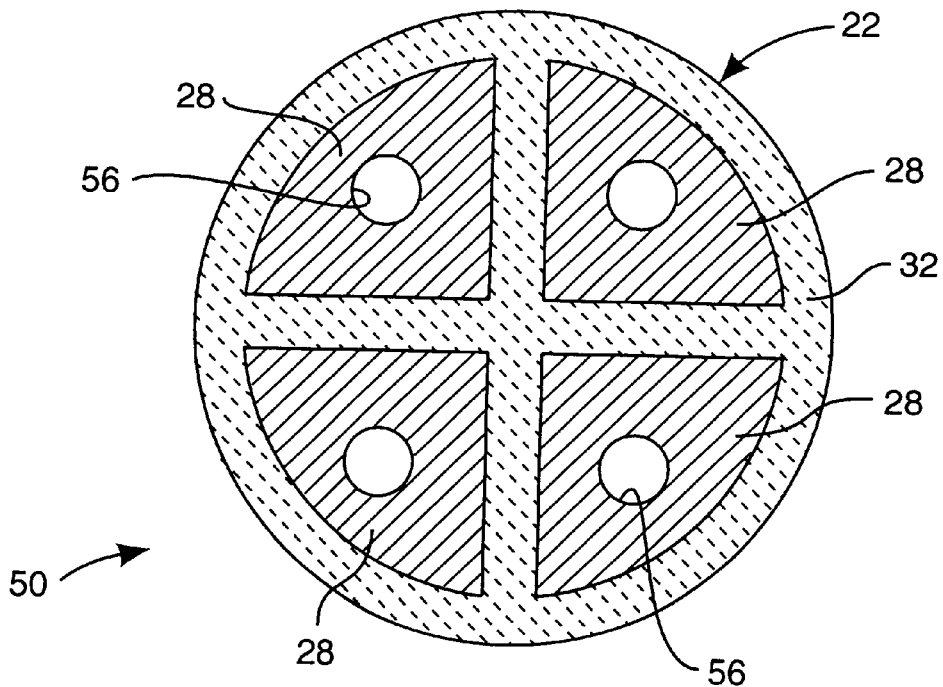
FIG. 5 is a sectional view taken generally along the line 5—5 of FIG. 4, illustrating an active electrode plate pattern within a capacitor of the feedthrough terminal assembly.
Figure 6:
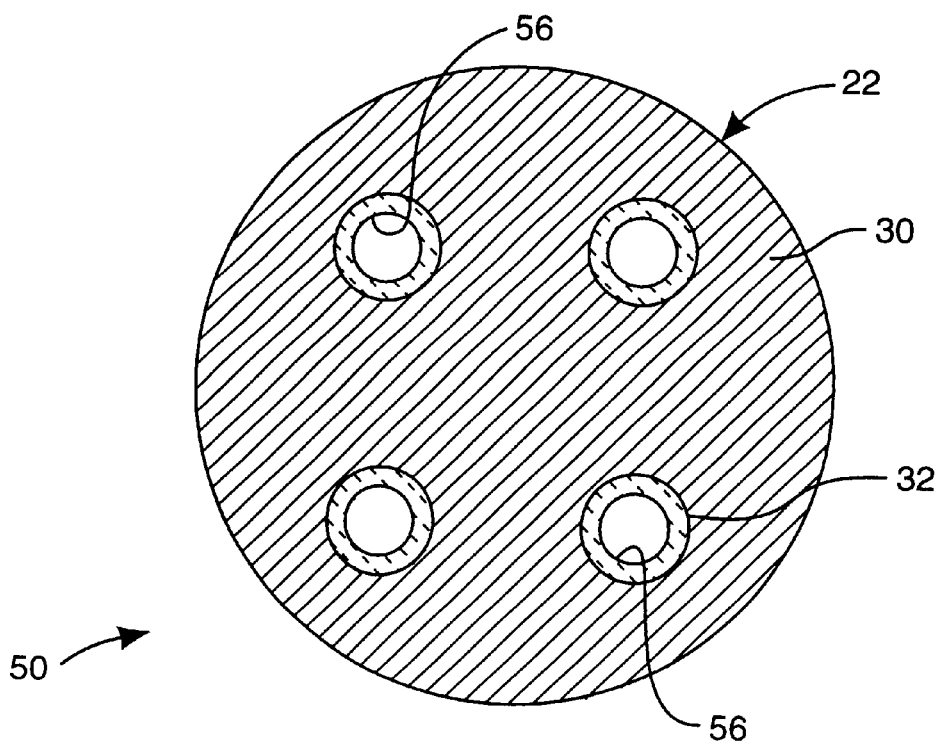
FIG. 6 is a sectional view taken generally along the line 6—6 of FIG. 4, illustrating a ground electrode plate pattern within the capacitor.

FIGS. 3 and 4 show the capture flange 58 coming approximately one-third to one-half the way up the outside diameter of the feedthrough capacitor 22. This flange 58 provides a convenient space in which to make an electrical connection between the capacitor outside diameter termination and the flange. Preferably, the capture flange 58 is titanium for use in an implantable medical device such as a cardiac pacemaker, implantable defibrillator, cochlear implant, neurostimulators, or the like. The insulator 60 material would be alumina ceramic, or glass, or other suitable material that would provide hermeticity and protection against body fluids. The lead wires 26 would be of noble material to provide corrosion resistance to body fluid (like platinum, niobium, or tantalum).

FIGS. 7 and 8 show one embodiment in which a feedthrough capacitor 22 is combined with a hermetic seal in such a way as to leave a space large enough for a conductive thermal-setting material 42, such as a conductive polyimide, to be automatically injected into the space between the capacitor 22 outside diameter and the capture flange 58. FIG. 7 indicates that the lead attachment would be done by a solder joint which can be done in a fluxless or inert gas atmosphere, such as a tunnel kiln or moving-belt hot-plate kiln.

Recent studies have indicated that during installation into the titanium can of an implantable medical device by laser welding, the outer diameter of the capacitor 22 indeed gets very hot and must be electrically connected with a material such as a polyimide which is not affected by temperatures at 300–500° C. However, these studies have also indicated that the temperature at the lead 26 does not get nearly as hot as long as the capacitor is not surrounding by thermally conducting materials as in the '551 patent. Accordingly, a high temperature solder such as AG1.5 or 10-88-2 (common trade names for Kester solders) can be used. These solders have a high lead content which gives them a very high melting point (approximately 300° C.). The high lead content makes for a malleable joint which will withstand the rigors of high temperatures and thermal shock. There are a number of other solders suitable for such application.

Again with reference to FIGS. 7 and 8, the outside diameter or outside perimeter attachment does not have to be continuous (360°). As shown in FIG. 8, the outside circumference attachment for a quad-polar capacitor 22 can be in four quadrants as indicated. Leaving an airspace 68 between the capacitor 22 and the insulator 60 allows for convenient helium leak detection (i.e. an open pathway by which helium gas can readily be detected in a standard leak test fixture). Alternatively, the capacitor 22 may be co-bonded or sealed to the alumina ceramic insulator 60 as shown in FIG. 4. In either case, the capture flange 58 provides for a convenient method of dispensing and containing the conductive thermal-setting material 42, solder, braze material, or a like brazing compound.

The assembly of FIG. 7 is particularly convenient for production automation. The automation steps include the following:

1. Shaker load the hermetic seal and titanium flange 34 into a holding fixture which could have as many as 100–500 locating holes.

2. Use a robot dispenser to dispense a partial or full O-ring seat 70 of non-conductive, high-temperature, thermal-setting material, such as a non-conductive polyimide (alternatively a robot could dispense a braze compound, solder preform, solder paste or the like).

3. The capacitor element 22 is shaker loaded into position on top of the non-conductive O-ring seat 70. A mating fixture with springs or sliding weights is then brought to bear to put a downward weight (or a downward pressure) on the capacitor 22 which seats it into the non-conductive, thermal-setting O-ring seat 70. This assembly is then put into an oven so that the non-conductive O-ring 70 is cured, which firmly seats the capacitor 22. This O-ring seal is further important in that this prevents the outside diameter conductive thermal-setting material from creeping underneath the capacitor and getting down under the air space. It is important that this non-conductive O-ring 70 will form a complete seal such that conductive particles will not migrate either through dispensing, centrifuging or through dendritic migration underneath the capacitor or between the capacitor 22 and the hermetic seal 66.

4. Use an automated robot dispenser to dispense the conductive thermal-setting material 42 between the outer diameter of the capacitor 22 and the titanium capture flange 58. In the embodiment of FIG. 10, the capture flange 58 has a convenient countersink 72 to facilitate the automated dispensing (alternatively a robot could dispense a braze compound, solder preform, solder paste or the like).

5. After the conductive thermal-setting material 42 is dispensed the entire assembly is put into a centrifuge. The centrifugal forces are used to pack the conductive thermal-setting material 42 into place and make sure that it is free of air voids. The centrifuging also has the affect of densifying the conductive material such that its resistivity and high frequency performance improve as the conductive particles move closer together. Another way of stating this is that since the conductive particles that are loaded within the conductive polyimide have a higher mass, they will tend to be driven to the bottom due to centrifugal forces. Accordingly, the solvents and the polyimide material will tend to come out on top. What results is a wetted conductive particle which when densely packed makes for a highly effective and low impedance high frequency RF connections. This step may have to be repeated; that is, after centrifuging and initial cure, the entire fixture holding all the parts can be put back into the robotic dispenser to have more conductive polyimide added. This is necessary in some cases where an air bubble has been trapped, and after centrifuging insufficient material is present. These steps can of course be repeated a number of times until sufficient packing is achieved.

6. Cure the conductive thermal-setting material 42 around the outer diameter of the capacitor 22. This is typically done for conductive polyimide at 300° C. which ensures that the material is above its glass transition point.

7. Make the electrical connection between the capacitor 22 inside diameter and the feedthrough lead wires 26. This can be accomplished automatically in a number of ways. For example, it can be combined with the step above, wherein conductive thermal-setting material 42 is automatically dispensed into the capacitor. This can be facilitated by radiusing the edges of the capacitor as indicated in FIGS. 9 and 10. Tumbling the capacitor 22 in either the green or the fired state has the effect of rounding off (radiusing) all sharp corners. This radius will appear on the capacitor 22 outside diameter as well as at the inner diameter (ID) or feedthrough holes. By providing a radius at the feedthrough hole, this makes it easier to dispense a conductive thermal-setting material into the ID cavity. An added benefit of providing a radius on the outside diameter of the capacitor 22 is that it makes the capacitor less subject to cracking and mishandling damage. A sharp corner or knife-edge type corner on a brittle barium-titanate ceramic capacitor can be problematic in that if it is bumped with a hard object or tweezers, it is very easy to fracture or break off this corner. Accordingly, the radiusing has two benefits, i.e., making the capacitor less subject to damage and also providing for a convenient method of dispensing either a thermal-setting conductive material or injection of a conductive solder paste. Other materials will be obvious to one skilled in the art, including various brazing materials, solder compounds, welding compounds, conductive glass frit, and the like.

8. An alternate automated assembly process for electrically and mechanically joining the capacitor feedthrough holes 56 to their corresponding lead wires 26. These steps would include the shaker loading of solder preforms onto the leads or using a robot to dispense a conductive solder paste and then running the entire fixture through an inert atmosphere soldering device such as a box soldering kiln, a Sikama type moving hotplate inert atmosphere kiln, or a tunnel soldering system with a moving belt such as that manufactured by BTU. The advantages of manufacturing this solder joint in an inert atmosphere is reduced oxidation and the ability to use either no-flux or a no clean flux.

This completes the basic assembly of the ceramic capacitor 22 to the hermetic seal pin assembly 24 to make it into a single homogeneous unit. It is now ready for electrical testing and shipment to customers.

FIGS. 9 and 10 show an embodiment where there is no air space between the capacitor 22 and the alumina insulator 60. In FIG. 10 a capacitor 22 is bonded to the alumina 60 by means of a non-conductive thermal-setting washer 70 such as a non-conductive polyimide. This non-conductive polyimide washer 70 can be produced in a number of shapes convenient for automated loading. In FIG. 10 the capture flange 58 has been spaced from the outside diameter of the capacitor in such a way as to leave sufficient space for automated dispensing of the non-conductive thermal-setting material. As described in U.S. patent application Ser. No. 08/969,480 now U.S. Pat. No. 6,008,980, the ceramic capacitor may be co-bonded to a hermetic insulator such as alumina, or the ceramic capacitor itself can become its own hermetic seal.

EMI testing and Network Analyzer testing has indicated that the capacitor electrode plates are sufficiently grounded by the external metallization provided that metallization is sufficiently thick. Previous experiments with sputtered terminations indicate that the sputtered termination must be very thick so that the outside diameter termination be of low impedance, but also thick enough to effectively absorb and reflect incident electromagnetic energy. Accordingly, the capacitor 22 of FIG. 7 is effective with an outside capture flange 58 that comes up the outside of the capacitor by approximately one quarter to three-quarters the way up the perimeter of the capacitor. In this way, the high frequency attenuation characteristics of the capacitor 22 are preserved while at the same time providing for convenient automated dispensing of materials to effect the connection between the outside diameter of the capacitor and its surrounding flange 58.

A number of alternative embodiments will be obvious to one skilled in the art. These include replacement of the alumina insulator 60 in FIG. 7 with various other materials such as compression glass seals, fusion glass seals, or the capacitor itself as described in U.S. patent application Ser. No. 08/969,480 now U.S. Pat. No. 6,008,980. Also, the flange 58 material may be made of a number of materials including titanium, stainless steel, cold-rolled steel, and others. There are also a wide range of alternative lead materials that can be used, particularly in non-medical implant applications. These include copper leads, alloy 52, Kovar leads, nickel leads, and the like. There are also a variety of supplemental plating materials that can be used. For example, if the flange 58 is made of cold-rolled steel and the leads are made of copper, then both of these could be subjected to nickel and then electro-tin plating in accordance with various specifications such as MIL-T-10727.

There are also a variety of capacitor shapes which are readily adaptable to automation using the capture flange 58. This includes rectangular feedthrough capacitors.

From the foregoing it will be appreciated that a novel ceramic feedthrough capacitor assembly which also forms a hermetic seal is provided for shielding and decoupling of a conductive terminal pin or lead of the type used, for example, in an implantable medical device such as a cardiac pacemaker or cardioverter defibrillator, to prevent the passage of externally generated electromagnetic (EM) fields such as interference signals caused by additional cellular phones. By integration of the ceramic feedthrough capacitor and hermetic seal into a single unit, the costly separate hermetic terminal subassembly is eliminated. Moreover, the assemblies described above may be utilized in connection with a unipolar feedthrough filter capacitor as well as multiple feedthrough filter capacitors provided in a substantially coplanar array within a common base structure. The use of a capture flange facilitates assembly by automation, and overcomes common undesirable attributes of other feedthrough filter terminals found in the prior art.

Although several embodiments of the invention have been described in detail for purposes of illustration, various further modifications may be made without departing from the spirit and scope of the invention. Accordingly, the invention is not to be limited, except as by the appended claims.

What is claimed is:

1. An EMI filter feedthrough terminal assembly, comprising:
    at least one conductive terminal pin;
    a feedthrough filter capacitor having first and second sets of electrode plates and a passageway through which the terminal pin extends in conductive relation the first set of electrode plates; and
    a conductive substrate through which the terminal pin passes in non-conductive relation, the conductive substrate including a capture flange having a height that less than an axial thickness of the capacitor and configured to at least partially surround an outer periphery of the capacitor.

2. The assembly of claim 1, wherein the height of the capture flange is one-quarter to three-quarters of the axial thickness of the capacitor.

3. The assembly of claim 1, wherein the second set of electrode plates is conductively coupled to the capture flange.

4. The assembly of claim 3, including a conductive material disposed between the outer periphery of the capacitor and the capture flange, to conductively couple the second set of electrode plates to the conductive substrate.

5. The assembly of claim 4, wherein the conductive material is a thermal-setting material taken from the group of conductive epoxy, conductive polyimide, or solder paste, a solder preform, a solder paste, or a braze alloy.

6. The assembly of claim 1, including an insulator supported by the conductive substrate through which the at least one terminal pin passes, the insulator being spaced from a face of the capacitor to form an air gap therebetween.

7. The assembly of claim 6, wherein the capture flange entirely surrounds the outer periphery of the capacitor, and wherein the assembly includes a conductive material disposed between discrete segments of the outer periphery of the capacitor and the capture flange.

8. The assembly of claim 6, including a first noble metal hermetic terminal seal joint between the terminal pin and the insulator, and a second noble metal hermetic seal joint between the insulator and the conductive substrate.

9. The assembly of claim 1, wherein the capture flange includes a countersink to facilitate robotic dispensing of a thermal-setting material between the capacitor and the capture flange.

10. The assembly of claim 9, wherein peripheral edges of the capacitor are axially rounded.

11. The assembly of claim 1, including a first noble metal hermetic terminal seal joint between the terminal pin and the feedthrough filter capacitor, and a second noble metal hermetic seal joint between the feedthrough filter capacitor and the conductive substrate.

12. An EMI filter feedthrough terminal assembly, comprising:

at least one conductive terminal pin;

a feedthrough filter capacitor having first and second sets of electrode plates and a passageway through which the terminal pin extends in conductive relation with the first set of electrode plates;

a conductive substrate through which terminal pin passes in non-conductive relation, the conductive substrate including a capture flange having a height that is less than an axial thickness of the capacitor and configured to at least partially surround an outer periphery of the capacitor, wherein the second set of electrode plates is conductively coupled to the capture flange; and an insulator supported by the conductive substrate through which the at least one terminal pin passes, the insulator being positioned adjacent to a face of the capacitor.

13. The assembly of claim 12, wherein the insulator is spaced from the face of the capacitor to form an air gap therebetween.

14. The assembly of claim 13, wherein the capture flange entirely surrounds the outer periphery of the capacitor, and wherein the assembly includes a conductive material disposed between discrete segments of the outer periphery of the capacitor and the capture flange.

15. The assembly of claim 14, including a first noble metal hermetic terminal seal joint between the terminal pin and the insulator, and a second noble metal hermetic seal joint between the insulator and the conductive substrate.

16. The assembly of claim 13, wherein the height of the capture flange is one-quarter to three-quarters of the axial thickness of the capacitor.

17. The assembly of claim 16, including a thermal-setting conductive material disposed between the outer periphery of the capacitor and the capture flange, to conductively couple the second set of electrode plates to the conductive substrate.

18. The assembly of claim 12, including a first noble metal hermetic terminal seal joint between the terminal pin and the feedthrough filter capacitor, and a second noble metal hermetic seal joint between the feedthrough filter capacitor and the conductive substrate.

19. The assembly of claim 12, wherein the capture flange includes a countersink to facilitate robotic dispensing of a thermal-setting material between the capacitor and the capture flange, and wherein peripheral edges of the capacitor are axially rounded.

* * * * *

Disclaimer 6,275,369 — Robert A. Stevenson, Canyon Country, CA; Donald K. Haskell, Minden, NV; Richard L. Brendel, Carson City, NV. EMI FILTER FEED-THROUGH TERMINAL ASSEMBLY HAVING A CAPTURE FLANGE TO FACILITATE AUTOMATED ASSEMBLY. Patent dated Aug. 14, 2001. Disclaimer filed Feb. 10, 2003, by the assignee, GreatBatch-Sierra, Inc.

Hereby enters this disclaimer to claims 1-6, 8, 11, 12, 13, 16, 17 and 18 of said patent.

*(Official Gazette, August 26, 2003)*